US008349591B2

(12) United States Patent
Desbarats et al.

(10) Patent No.: US 8,349,591 B2
(45) Date of Patent: Jan. 8, 2013

(54) METHOD AND APPARATUS FOR PRODUCING ALCOHOL OR SUGAR USING A COMMERCIAL-SCALE BIOREACTOR

(75) Inventors: Andrew Desbarats, Aurora (CA); Michael Erhart, Phillipsburg, KS (US); Joe Kreutzer, Phillipsburg, KS (US); Kevin Morgan, Phillipsburg, KS (US); Vince Yacyshyn, Calgary (CA)

(73) Assignee: Scientek LLC, Phillipsburg, KS (US)

(*) Notice: Subject to any disclaimer, the term of this patent is extended or adjusted under 35 U.S.C. 154(b) by 0 days.

(21) Appl. No.: 13/119,727

(22) PCT Filed: Oct. 13, 2009

(86) PCT No.: PCT/US2009/060409
§ 371 (c)(1),
(2), (4) Date: Mar. 18, 2011

(87) PCT Pub. No.: WO2010/045168
PCT Pub. Date: Apr. 22, 2010

(65) Prior Publication Data
US 2011/0207176 A1    Aug. 25, 2011

Related U.S. Application Data

(60) Provisional application No. 61/105,906, filed on Oct. 16, 2008, provisional application No. 61/107,383, filed on Oct. 22, 2008, provisional application No. 61/139,678, filed on Dec. 22, 2008, provisional application No. 61/229,855, filed on Jul. 30, 2009.

(51) Int. Cl.
*C12P 19/00* (2006.01)
*C12P 7/06* (2006.01)
*C12P 7/14* (2006.01)

(52) U.S. Cl. .................. 435/72; 435/161; 435/162
(58) Field of Classification Search ............ 435/72, 435/161, 162
See application file for complete search history.

(56) References Cited

U.S. PATENT DOCUMENTS

| | | | |
|---|---|---|---|
| 3,819,528 | A | 6/1974 | Berry |
| 4,204,041 | A | 5/1980 | Bailey |
| 4,250,263 | A | 2/1981 | Winans |
| 4,548,727 | A | 10/1985 | Shaer |
| 5,135,853 | A | 8/1992 | Dziewulski |
| 5,888,781 | A * | 3/1999 | Sierks et al. ........... 435/99 |
| 6,582,606 | B2 | 6/2003 | Laustsen |
| 6,797,508 | B1 | 9/2004 | Holker |
| 7,157,416 | B2 * | 1/2007 | Becker et al. ........... 510/393 |
| 7,892,805 | B2 | 2/2011 | Saville |
| 2004/0259219 | A1 | 12/2004 | Saville |
| 2005/0239181 | A1 | 10/2005 | Lewis |
| 2006/0134766 | A1 * | 6/2006 | Saville et al. ........... 435/174 |
| 2008/0152638 | A1 | 6/2008 | Kelemen |
| 2008/0248540 | A1 | 10/2008 | Yang |
| 2011/0008830 | A1 * | 1/2011 | Desbarats et al. ........... 435/68.1 |

FOREIGN PATENT DOCUMENTS

| | | |
|---|---|---|
| GB | 1082370 | 9/1967 |
| GB | 1091347 | 11/1967 |
| GB | 1507792 | 4/1978 |
| JP | 560003631 | 1/1981 |
| JP | 560003632 | 1/1981 |
| JP | 60092433 | 5/1985 |
| RO | 90071 | 8/1986 |
| WO | 2005117948 A1 | 12/2005 |

OTHER PUBLICATIONS

Zawistoska et al. (Immobilized Metal Affinity Chromatography of What α-Amylases. Cereal Chemistry vol. 65, No. 5, 1988.*
Schuster, The Effect of Charcoal Treatment on Microsomal Cytochrome P-450, FEBS letters, vol. 74, Feb. 1977, p. 107-110.
Aikat, Decolorization and Purification of Crude Protease from *Rhizopus oryzae* by Activated Charcoal and its Electrophoretic Analysis, Biotechnology Letters, vol. 23, 2001, p. 295-301.
Bailey, Immobilization of Blucoamylase and Glucose Oxidase in Activated Carbon: Effects of Particle Size and Immobilization Conditions on Enzyme Activity and Effectiveness, Biotechnology and Bioengineering, vol. 25, 1983, p. 1923-1935.
http:www.usm.maine.edu/~rhodes/biochemLab/text/HdtPurLys/DHTPurLys03.html.
http:www.ap-lab.com/circular_dichroism.htm.
Shenoy, Fungal Glucoamylases, Journal of Bioscience, vol. 7, Jun. 1985, p. 399-419.
Gibeaut, Synthesis of (1-3), (1-4)-B-D-glucan in the Golgi Apparatus of Maize Coleoptiles, Proceedings of the National Academy of Sciences of the U.S., vol. 90, p. 3850-3854, May 1993.
Rani, Preparation and Characterization of Amyloglucosidase Adsorbed on Activated Charcoal, , Journal of Molecular Cataysis B Enzymatic, vol. 10, No. 5, Oct. 2000, p. 471-476.
Cho, Immobilization of Enzymes on Activated Carbon: Properties of Immobilized Glucoamylase, Glucose Oxidase, and Gluconolactonase, Biotechnology and Bioengineering, vol. 20, No. 10, 1978, p. 1651-1665.
European Office Action mailed Jul. 29, 2008 in connection with U.S. application (now USPN 7,892,805) having same inventor.
International Search Report and Written Opinion (mailed Dec. 10, 2009).
"Activated Carbon," National Organic Standards Board Technical Advisory Panel Review Compiled by OMRI for the USDA National Organic Program, Aug. 14, 2002, pp. 1-23.
Milcent, et. al., "Clarification of Lactic Acid Fermentation Broths," Separation and Purification Technology, 22-23 (2001) pp. 393-401.
Tsun, et. al., "Recovery and Purification of Thuringiensin from the Fermentation Broth of *Bacillus thruingienisis*," Bioseparation 7: pp. 309-316 (1999).
Liljedahl, "Evaluation of Chromatagraphic Media for Membrane Protein Purification," MSc. Thesis, Uppsala University School of Engineering, 2001, pp. 1-20.

(Continued)

*Primary Examiner* — Karen Cochrane Carlson
*Assistant Examiner* — Natalie Moss
(74) *Attorney, Agent, or Firm* — Jeffrey S. Melcher; Manelli Selter, PLLC

(57) ABSTRACT

Provided is a method of producing alcohol or sugar in a commercial-scale bioreactor using a reformulated commercial enzyme preparation. Also provided is a bioreactor modified to practice the method.

20 Claims, 1 Drawing Sheet

OTHER PUBLICATIONS

Kerkhoff et al., "Solubilization, Partial Purification and Photolabeling of the Integral Membrane Protein Lysophospholipid:acyl-CoA Acyltransferase (LAT)," Eur. J. Biochem, 267, 6339-6345 (2000).

Cornell lab manual for BIOBM330. http://instruct1.cit.cornell.edu/Courses/biobm330/protlab/Strategy.html.

Instructional materials for the MATC Biotechnology program in Madison, WI http://matcmadison.edu/biotech/resources/proteins/labManual/chapter_1.htm.

Wingfield et al., Purification and characterization of a methionine-specific aminopeptidase from *Salmonella typhimurium*, Eur. J Biochem. 180.23-32 (1989).

Mackay et al., "Identification and Isolation of a 155-KDa Protein with Neuropathy Target Esterase Activity," Fundamental and Applied Toxicology, vol. 30, pp. 23-30, (1996).

Pimenov et al., "The Adsorption and Deactivation of Microorganisms by Activated Carbon Fiber," Separation Science and Technology 36(15), 3385-3394, (2001).

Hydamaka et al., "Control of Color Problems During Recycling of Food Process Waters," Food Science Department at the University of Manitoba, pp. 237-256.

Kelly, et. al., "The Use of Circular Dichroism in the Investigation of Protein Structure and Function," Curr. Protein and Peptide Sci., 1, 349-384, (2000).

Lendenmen, et. al., "2-Aminophenol 1,6-Dioxygenase: a Novel Aromatic Ring Cleavage Enzyme Purified from *Pseudomonas pseudoalcaligenes* JS45," J. Bacteriol., pp. 6227-6232, (1996).

Chen et al., "D-Ribulose-5-Phosphate 3-Epimerase: Cloning and Heterologous Expression of the Spinach Gene, and Purification and Characterization of the Recombinant Enzyme," Plant Physiol. 118: 199-207, (1998).

Walsh, "Proteins: Biochemistry and Biotechnology," Wiley, West Sussex, England. pp. 156-161 (2002).

Sadana, "Bioseparation of Proteins," Academic Press, San Diego, pp. 1-15, 135, 136, 178, 187, and 245 (1998).

Ladisch, et. al., "Protein Purification: From Molecular Mechanisms to Large Scale Processes," ACS Symposium Series 427 (1990).

Bailon, et. al., "Recovery of Recombinant Proteins by Immunoaffinity Chromatography", pp. 150-167. (Note-included in Ladish, ref. No. 18 above).

Harrison, "Protein Purification Process Engineering," Marcel Dekker, New York, pp. 6, 7, 44, 45, 52, 53, 128-131, 136, 137, 146, 147, 152-155, 172-175, 210 and 211(1994).

Stein, "Fundamentals of Protein Biotechnology," Marcel Dekker, New York, pp. 145, 161, and 162 (1990).

Wheelwright, "Protein Purification: Design and Scale up of Downstream Processing," Hanser Publishers, Munich, pp. 32, 33, 62, 63, 80, 82, 172, and 186 (1991).

Davis, "Covalent immobilisation of laccase on activated carbon for phenolic effluent treatment", Appl Microbiol Biotechnol (1992) 37:474-479.

Sotiropoulou, et. al., "Lowering the detection limit of the acetylcholinesterase biosensor using a nanoporous carbon matrix", Analytica Chimica Acta 530 (2005) 199-204.

Kibarer, et. al., "Optimization studies on the features of an activated charcoal-supported urease system, Biomaterials". vol. 17, No. 15, pp. 1473-1479. (1996).

Roth, et. al., β-Galactosidases (*Escherichia coli*) with Double Substitutions Show That Tyr-503 Acts Independently of Glu-461 but Cooperatively with Glu-537, Journal of Protein Chemistry, vol. 22, Nos. 7/8, Nov. 2003.

Majunath, et. al., "Fungal Glucoamylases," J. Appl. Biochem., vol. 5, pp. 235-260 (1983).

International Preliminary Report on Patentability (issued Apr. 19, 2011) and Written Opinion of Searching Authority (mailed Dec. 10, 2009).

European Office Action issued May 22, 2012 in corresponding application.

Teotia, "Reversibly soluble macroaffinity ligand in aqueous two-phase separation of enzymes," Journal of Chromatography, Elsevier Science Publishers, B.V. NI. vol. 923, No. 1-2 (Jul. 20, 2001) pp. 275-280.

Meyer, "Anthocyanin Productionfrom *Caccinium pahalae*: Limitations of teh Physical Microenvironment," Journal of Biotechnology, Elsevier Science Publishers, Amsterdam, NL, vol. 93, No. 1 (Jan. 1, 2002) pp. 45-57.

Reshmi, "Enhanced activity and stability of alpha-amylase immobilized on alumina," Catalysis Communications, Elsivier Science, Amsterdam, NL, vol. 7, No. 7 (Jul. 1, 2006) pp. 460-465.

Hoshino, "Continuous ethanol production from raw starch using a reversibly soluble-autoprecipitating amylase and flocculating yeast cells," Journal of Fermentation and Bioengineering, Society of Fermentation Technology, JP. vol. 69, No. 4 (Jan. 1, 1990) pp. 228-233.

* cited by examiner

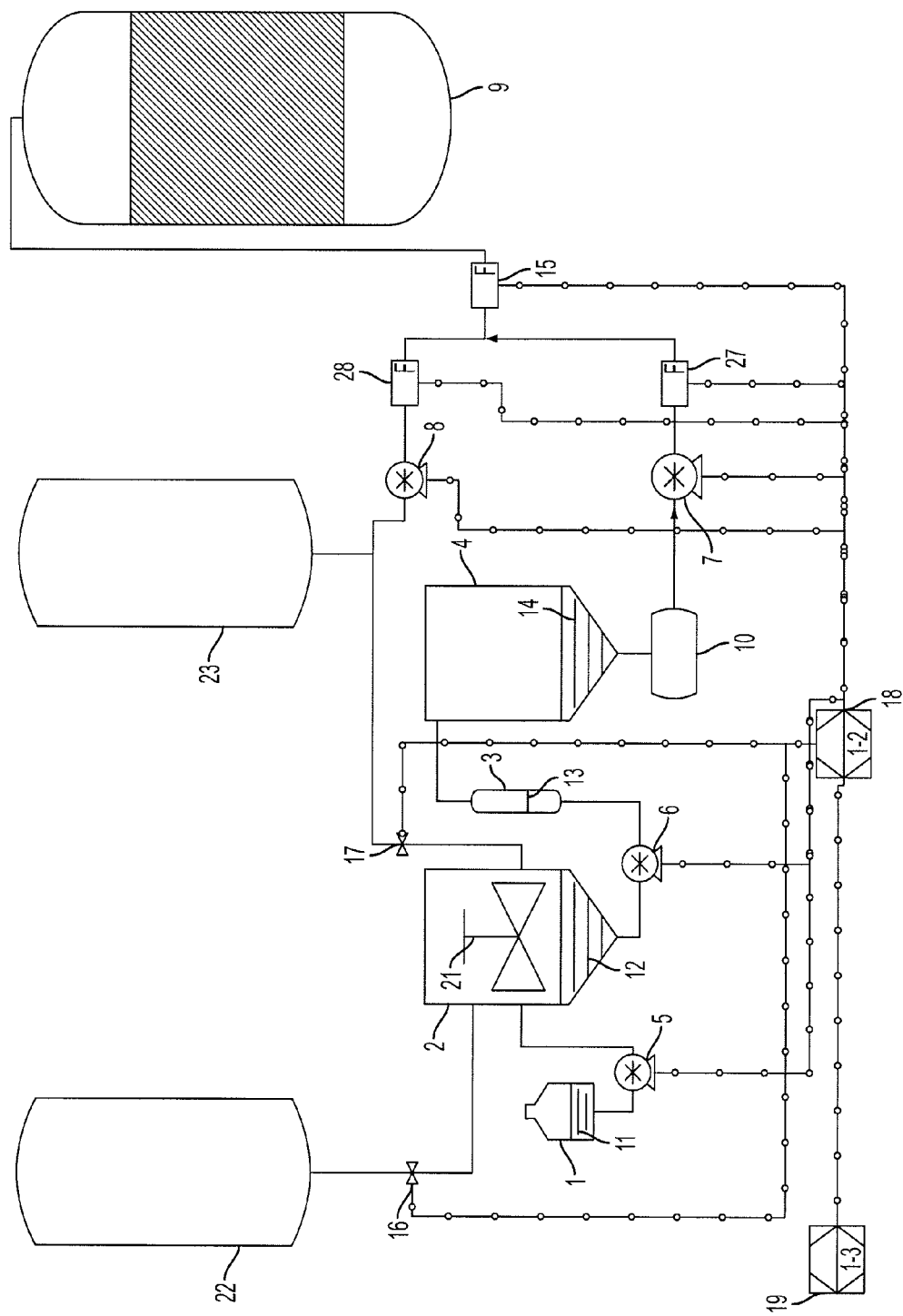

METHOD AND APPARATUS FOR PRODUCING ALCOHOL OR SUGAR USING A COMMERCIAL-SCALE BIOREACTOR

This application claims priority to U.S. Patent Application Ser. Nos. 61/105,906, filed 16 Oct. 2008; 61/107,383, filed 22 Oct. 2008; 61/139,678, filed 22 Dec. 2008; and 61/229,855, filed 30 Jul. 2009, the complete disclosures of which are incorporated herein by reference.

FIELD OF THE INVENTION

The invention relates to commercial-scale processes for producing alcohol or sugar in a bioreactor using a reformulated commercial enzyme preparation and apparatuses for practicing the processes.

BACKGROUND OF THE INVENTION

It is well known that enzymes in liquid media can be stabilized using compounds such as metal halide salts (U.S. Pat. No. 7,157,416), alcohol ethoxylates (U.S. Pat. No. 4,548,727), aliphatic glycols and 1,3 propanediol (U.S. Pat. No. 3,819,528). The aim of these stabilization techniques is to stabilize substantially against loss of activity during storage. The ability to stabilize enzymes has been useful for users of industrial enzymes. Onsite storage in large vessels can reduce shipping costs, decrease the space required to store containers of enzyme and reduce the risk of enzyme shortages. Stabilization also reduces the risk of bacterial infections caused by microorganisms in the enzyme solution. For enzyme users that employ bioreactors and reagents with biological activity, such as producers of fuel ethanol, these infections can reduce product and co-product yield, impair process efficiency and increase operating costs incurred to fight the infections.

Currently, common industrial enzymes such as proteases, group 3 hydrolases and lipases are mixed with both metal halide salts such as sodium chloride and polyols, such as glycerol, before shipping to customers. Other compounds used for stabilization include antioxidants and amino acids such as methionine, which prevents oxidation of surface amino acids.

The following prior art provides examples of effective techniques for enzyme stabilization that have afforded substantial benefits to users of industrial enzymes. For example, Vermousek et al. (CS 210467) shows a powder mixture of urease with buffering, complexing and antibacterial agents that has practically infinite stability. Kelemen et al. (U.S. published patent application No. 20080152638) describe a glucose oxidase enzyme with improved storage stability. Becker et al. (U.S. Pat. No. 7,157,416) describe enzyme-containing formulations, comprising a metal halide salt and a polyol, having improved stability and enzymatic activity in liquid medium, particularly protease enzymes. Jaber (WO/2005117948) describes a method of preparing a stabilized bulk solution of a monomeric protein which consists in providing a bulk of monomeric protein in a buffer solution and adding an excipient to the bulk where the excipient is selected from the group of bacteriostatic agents, surfactants, isotonicity agents, amino acids, antioxidants and combinations thereof. Jaber's method prefers IFN-beta as the monomeric protein.

It has become commonplace for users of industrial enzymes to add the entire cocktail of enzyme and polyol and metal halide salt stabilizers and other preservatives into a bioreactor. There are a number of reasons for this, including the expense associated with separating enzymes from their metal halide salt, polymeric stabilizers and the requirement to separate enzyme from salt, polymeric stabilizers immediately prior to addition to a bioreactor so as to minimize instability and bacterial growth. In addition, very little has been published about the effects of dissociating these enzymes from their stabilizers prior to use in a bioreactor.

Bioreactors are now well known. In general, a bioreactor is a vessel in which a biochemical reaction takes place. Commercial-scale bioreactors typically have a capacity of over 1000 gallons. In commercial scale ethanol plants, bioreactors in which starch and cellulose are hydrolysed with enzymes typically have a capacity of 20,000 to 100,000 gallons. Fermentation vessels, within which enzymes catalyze biochemical reactions and microorganisms use reaction intermediates to produce metabolites, typically have a capacity of 100,000 to 1,000,000 gallons. Conditions such as temperature, pressure, pH and solution viscosity are tightly controlled within bioreactors due to the sensitivity of biochemicals and microorganisms. For example bioreactors within which starch and cellulose are hydrolysed typically have temperatures in the range of 75 to 100 degrees Celsius for starch and 45 to 75 degrees Celsius for cellulose.

One of the problems with adding the entire commercial enzyme formulation to the bioreactor is that inorganic salts will often contribute to instability of certain enzymes at high temperatures. A study by Klibanov showed that inorganic salts such as KCl and $Na_2SO_4$ destabilize thermostable alpha-amylase at 90 degrees Celsius. In addition, ions of inorganic salts can pose problems downstream from the bioreactor in final products. This is a serious problem in ethanol used for transportation fuel. For example, a study by Galante-Fox et al. shows that chloride levels greater than 3.5 ppm (weight) in fuel ethanol can cause severe corrosion of steel, reducing the demand for these transportation fuel products and other grain and cellulose-derived products.

There is a large body of knowledge concerning the use of enzymes in organic solvents and the benefits of pretreating these enzymes prior to use in organic solvents. Klibanov has shown that pretreating lipases prior to use in organic solvents can substantially increase activity.

It is also widely accepted that high concentrations of polymeric compounds promote rigidity in the structure of enzymes with which they are mixed. Hydrating these enzymes has the opposite effect where enzymes become less rigid and more flexible. Klibanov has referred to this phenomenon as 'lubricating' the enzyme. Hydration takes advantage of the ability of water to form hydrogen bonds with functional groups of a protein molecule, which may have been bound to each other before addition of water.

One way to change the concentration of inorganic salts and polymeric stabilizers is to reformulate the enzymes prior to use. Studies by Zaks and Klibanov have shown that hydration of powdered enzymes, prior to reaction with substrate, results in a loosening up of the enzyme structure and, at certain levels, the onset of catalytic activity. Unfortunately, most industrial enzyme users prefer liquid enzyme solutions to powdered enzymes. Shipping, transferring and hydrating dry enzymes is not the most efficient way to use enzymes especially when liquid enzymes can be stabilized with polymeric materials.

While hydration of enzymes may induce flexibility in their structures, in separate studies, Klibanov and Won found that increasing the water content in organic solvents to the water solubility limit, caused enzyme agglomeration resulting in glue-like fibers devoid of catalytic activity. Therefore, while hydration has the benefits listed above, there are also practical issues limiting the ability of enzyme users to hydrate enzymes in organic solvents.

Commercial enzyme preparations also contain a high concentration of enzymes, between 5 mg/mL and 25 mg/mL. These commercial enzyme preparations, have the benefit of reducing the number of shipments and the required storage capacity in facilities that use industrial enzymes.

Liquid enzyme formulations are often dosed at 3 places in an ethanol plant;

1) The slurry system, where initial hydrolysis takes place. In a typical 40 million gallon per year dry-mill ethanol plant, alpha-amylase is often added at between 500 mg/min and 1200 mg/min
2) The liquefaction system, where secondary hydrolysis takes place. In a typical 40 million gallon per year dry-mill ethanol plant, alpha-amylase is often added at between 1000 mg/min and 2000 mg/min
3) The fermentation system, where final hydrolysis and fermentation of the product takes place. In a typical 40 million gallon/year dry-mill ethanol plant, the enzyme dose is in the range of between 60 and 120 Gallons in a 500,000 Gallon fermenter.

These dose ranges are adjusted accordingly for different plant capacities. For instance, 100 million gallon per year dry-mill ethanol plants require an alpha amylase dose in the range of 1250 mg/min and 3000 mg/min in the slurry system and between 2500 mg/min and 5000 mg/min in slurry and liquefaction respectively.

In addition, ethanol plants may produce ethanol from different types of feedstock. These feedstocks will vary in terms of the amount of ethanol produced per ton of feedstock. For example, dry mill ethanol plants typically produce between 2.5 and 2.9 Gallons per bushel of corn. The corn is milled and mixed with water in a ratio of between 28% and 38% solids. The theoretical ethanol yield for a ton of corn stover is 113 Gallons per dry ton. Currently, solids ratios for ethanol production from biomass sources such as corn stover are lower than solids ratios for ethanol production from corn and other grains and is typically between 8 and 20% solids.

However at high enzyme concentrations it is difficult to accurately dose low volumes of enzyme since, in the case of a 25 mg/mL protein, each milliliter contains 25 mg of protein, which may be more than one wants to dose over a particular time frame.

This problem is exacerbated by the polymeric stabilizers, which are characterized by high specific gravities. The combination of high specific gravity and high enzyme concentration makes it difficult to fine-tune dosing of industrial enzymes to bioreactors. Specialized pumps, capable of pumping high specific gravity liquids at low flow rates are expensive and there are limits to their accuracy.

Saville (U.S. published patent application No. 20040259219) showed that the activity of a group 3 hydrolase could be increased by diluting said group 3 hydrolase in water or an aqueous buffer and treating said hydrolase with activated carbon. Saville showed specifically that the activity increase was due to a reaction between the enzyme and the activated carbon. Saville's dilution step also reduces the concentration of salts and other preservatives, however, diluting with water or an aqueous buffer reduces the concentration of polymeric compounds to the point where ester-based or lactone-based polymers quickly form in the enzyme solution. Bacteria can grow on these polymers causing problems in bioreactors. These polymers coat the instrumentation and pipes, reducing flow and causing instrumentation to malfunction. In addition, increasing enzyme activity is not always desirable, for example in simultaneous saccharification and fermentation systems, an overly active glucoamylase enzyme will produce glucose at a rate that is detrimental to conversion of glucose to ethanol. These problems are exacerbated when the enzymes are diluted and treated with activated carbon in a central location, then delivered to enzyme users. Because Saville's purified enzymes are only stable for a short period of time, and Saville does not describe a way to purify enzymes on site and just-in-time, the invention by Saville is difficult to practice.

Laustsen (U.S. Pat. No. 6,582,606) teaches microfiltration of an enzyme solution using small amounts of activated carbon. While Laustsen does not teach increased activity, Laustsen does claim that microfiltration with activated carbon increases process capacity and reduces fouling.

However Laustsen's method teaches only a 1:1 and a 1:1.5 dilution of the enzyme solution prior to treatment with activated carbon. The specific gravity of an enzyme solution diluted 1:1 or 1:1.5 is still much higher than 1.0 g/mL, and poses problems for accurate dosing. In addition, Laustsen's process requires expensive microfiltration equipment, and which requires specialized expertise that may not be present in a carbohydrate processing operation. Finally, Laustsen's process specifies microfiltration of solids from liquid formulations. There are no solids in the commercial enzyme that is delivered to industrial users of Group 3 hydrolases in liquid form, therefore one skilled in the art would find little use in repeating the microfiltration of liquid enzymes as per Laustsen's invention.

Lab-scale assay demonstrates a significant decrease in enzyme activity for reformulated vs. non-reformulated enzymes, with reformulated enzymes being those having the concentration of enzyme and stabilizers reduced by dilution with water or aqueous buffer solutions. Since full scale production runs cost upwards of $150,000, those skilled in the art would avoid testing such reformulated enzymes on full scale production runs.

In light of the prior findings on loss of catalytic activity from over-hydration of enzymes in an organic solvent, a person skilled in the art would not reformulate an enzyme prior to delivery to a bioreactor, especially since enzyme users can cost-effectively add the enzyme and the polymeric materials to a bioreactor with no adverse effect. In addition, in light of reduced stability, increased bacterial growth and polymer formation, a person skilled in the art would hesitate to dilute an enzyme solution with aqueous buffer prior to adding to a bioreactor. Further, commercial enzyme solutions are free of solids, therefore one skilled in the art would not practice the mixing of commercial enzyme solutions and activated carbon prior to microfiltration through a membrane. Commercial enzyme preparations are already filtered through such membranes before they are received by the enzyme user; there would be substantial expense with little associated benefit.

There is a need to reformulate industrial enzymes to reduce the concentration of salts and other preservatives, decrease the specific gravity of the commercial enzyme preparation for accurate dosing, maintain stability of the solution for a timeframe long enough to deliver the reformulated solution to a bioreactor, prevent polymer growth and provide an enzyme solution with a desirable level of activity for the intended use. An effective reformulation method will also allow enzyme producers to provide higher strength commercial enzyme formulations to further reduce shipping costs and storage capacity requirements, both at the enzyme supplier facility and at the enzyme user facility. Users of commercial enzyme preparations can adapt to these higher strength enzyme formulations without acquiring new, more expensive and possibly less accurate pumps.

SUMMARY OF THE INVENTION

It is the primary object of the present invention to provide a process for hydrating stabilized enzyme preparations on-site and enabling just-in-time delivery of reformulated enzymes to a bioreactor which improves the cost-effectiveness of said stabilized enzyme preparations.

It is a further object to provide an apparatus for hydrating stabilized enzyme preparations on-site and enabling just-in-time delivery of reformulated enzymes to a bioreactor.

It is a further object to provide an automated system that decreases the specific activity of certain Group 3 hydrolases at 37 degrees Celsius.

It is a further object to provide an automated system that improves the thermalstability of certain Group 3 hydrolases at about 90 degrees Celsius.

A further object is to reduce the specific gravity of stock enzyme solutions prior to addition to a bioreactor to facilitate pumping and enable more accurate enzyme dosing.

A further object is to reduce the chloride concentration of the stock enzyme solution to reduce the total chloride concentration in the bioreactor and in downstream products.

It is a further object to provide an automated apparatus that lowers the minimum effective dose of the enzyme in the bioreactor while maintaining equivalent production of reaction products.

It is a further object to provide a mechanism whereby a mixture of reformulated enzyme solution and non-reformulated enzyme solution can be mixed, in-line, and delivered accurately to a bioreactor and whereby any decrease in delivery of either the reformulated or the non-reformulated enzyme solution will be compensated for by a corresponding increase in delivery of the appropriate solution.

It is a further object to provide an automated and programmable system that can store desired ratios of stock enzyme and hydration buffer based on different levels of dry solids in the bioreactor, different types of feedstocks, different operating rates, different stock enzyme solutions, different concentrations of enzyme and other parameters that may be of use to bioreactor operators.

The present invention provides a process whereby a commercial enzyme preparation that has been stabilized with salts, and/or polymeric compounds and/or antioxidants is reformulated at the end-user's site. The reformulated enzyme has a low specific gravity relative to the commercial stabilized enzyme from which it is derived enabling more accurate dosing. The reformulation method uses a reformulating solution that maintains stability of the reformulated enzyme over a longer period of time than that provided by mere dilution with water or an aqueous solution. The invention also provides an apparatus necessary for on-site hydration and timely, accurate delivery of the reformulated enzyme solution to said bioreactor. This hydration should occur within 100 hours prior to addition of the reformulated enzyme to the bioreactor.

Provided is a method of producing alcohol or sugar in a commercial-scale bioreactor comprising:
  mixing a commercial enzyme preparation comprising at least one group 3 hydrolase that has been stabilized for shipment or storage with a dilute aqueous solution comprising a polymeric compound in a mixing vessel in a ratio of 1 part commercial enzyme preparation to at least 4 parts solution of the dilute aqueous solution to form a diluted enzyme solution;
  passing the diluted enzyme solution through a chamber containing at least one metal particulate matter or metal-impregnated particulate matter to produce a reformulated enzyme solution; and
  within 100 hours of production of the reformulated enzyme solution, transferring at least a portion of the reformulated enzyme solution to a commercial-scale bioreactor containing at least 20,000 gallons of at least one of starch or cellulose to produce an alcohol or sugar, wherein a total amount of enzyme in the form of the reformulated enzyme solution added to the bioreactor is at least 20% less than the amount of enzyme in the form of the commercial enzyme preparation that would have been required to produce an equivalent amount of alcohol or sugar.

Also provided is an apparatus for producing alcohol or sugar in a commercial-scale bioreactor, the apparatus comprising:
  a mixing vessel;
  a mixing device for mixing a solution in the mixing vessel;
  a source of aqueous buffer and disinfectant in communication with the mixing vessel;
  a source of stabilized enzyme preparation in communication with the mixing vessel;
  a storage vessel in communication with the mixing vessel; and
  at least one commercial-scale bioreactor having a capacity of at least 20,000 gallons in communication with the storage vessel.

On a commercial scale, the present invention provides a reduction of at least 20%, preferably at least 40%, and more preferably at least 60% of the total amount of enzyme in the form of the reformulated enzyme solution added to the bioreactor compared to the amount of enzyme in the form of the commercial enzyme preparation that would have been required to produce an equivalent amount of alcohol or sugar.

The process and apparatus have been shown to increase the accuracy of dosing concentrated, high specific gravity commercial enzyme preparations to a bioreactor.

BRIEF DESCRIPTION OF DRAWING

FIG. 1 shows a side view of an apparatus for reformulating stabilized enzyme preparations

DETAILED DESCRIPTION OF INVENTION

Lab-scale assays demonstrates a significant decrease in enzyme activity for reformulated vs. non-reformulated enzyme. In particular, lab-scale assays demonstrate significant decreases in enzyme activity when commercial enzyme solutions are reformulated by diluting with water or aqueous buffers, or when the concentration of stabilizers is reduced. Since full scale production runs using such enzyme solutions are very costly, upwards of $150,000, those skilled in the art would not test such reformulated enzyme solutions in a full scale production run.

However, when used on a full scale production run, reformulated enzyme solutions do not result in decreased enzyme activity as expected from the well known lab-scale assays, but rather result in significant unexpected increases in enzyme activity. In the production environment equivalent sugar production, as measured by fermentation profiles, indicate that the reformulation process improves the rate at which substrate is converted to product per unit mass of enzyme used. The conditions in the production environment may contribute to this effect, without being bound by any theory. In addition, the starch slurry is more viscous than the substrate solution in the standard lab-scale assay, creating differences in diffusion of enzyme molecules through the slurry. Further, the temperature of the starch slurry is much higher than that of the substrate solution in the standard lab-scale assay creating additional differences such as changes in solubility.

On a commercial scale, the present invention provides a reduction of at least 20%, preferably at least 40%, and more preferably at least 60%, of the total amount of enzyme in the form of the reformulated enzyme solution added to the bioreactor compared to the amount of enzyme in the form of the commercial enzyme preparation that would have been required to produce an equivalent amount of alcohol or sugar.

Commercial stabilized enzyme preparations are now well known, such as those provided by Novozymes and Genencor. Improving enzyme function in the bioreactor by reformulation prior to addition to said bioreactor can be effected according to the present invention using any desired commercial enzyme solution. Preferably, the enzyme comprises at least one group 3 hydrolase. A most preferred enzyme is amylase.

Typical commercial enzyme preparations contain a high concentration of polymeric compounds, dissolved salts, antioxidants, substrates and/or substrate analogs. These compounds stabilize commercial enzyme preparations in order for enzyme users to store large quantities on site, reduce transportation costs involved in shipping small quantities and ensure minimal bacterial growth over long periods of time. However commercial stabilized enzyme preparations must often be delivered accurately to bioreactors containing aqueous mixtures. It has been found that hydration of these commercial stabilized enzyme solutions according to the present invention can improve dosing accuracy and reduce the mass of enzyme required in the bioreactor.

Alpha-amylase enzymes are used at temperatures ranging from 75 to 95 degrees C. for the hydrolysis of starch and long-chain maltodextrins. As a result of the reformulation process described in the present invention, the reformulated alpha-amylase enzyme is more resistant to thermal and chemical denaturation than the commercial stabilized enzyme from which it is derived. As a result, the reformulated alpha-amylase with lower activity relative to the commercial stabilized enzyme solution from which it was derived, resists denaturation and is active for longer at high temperatures. Enzyme users therefore can reduce the amount of alpha-amylase used in high-temperature bioreactors. This is especially relevant for liquefaction bioreactors in dry-mill fuel ethanol plants were the residence time of the substrate is often more than one hour. By using the present invention, users of these commercial enzyme formulations can substantially reduce the cost of operating these bioreactors.

The inventions will now be explained with reference to the attached FIGURE without being limited thereto.

As shown in the drawing, the enzyme reformulation apparatus comprises an optional buffer vessel 1, a mixing vessel 2, a column containing a metal or metal-impregnated particulate matter 3, a storage vessel 4, an optional surge tank 10. The mixing vessel 2, the storage vessel 4, and surge 10 are constructed of 304 or 316 stainless steel but can be constructed of any desired material suitable to hold the solutions.

The buffer vessel 1 contains a polymeric compound or a mixture of water and polymeric compound. The desired final concentration of polymeric compound in mixing vessel 2 can be, for example between 2% by volume and 15% by volume, preferably between 5% and 10% by volume. The polymeric compound 11 can be pumped using a variable speed pump 5 to the mixing vessel 2 containing the necessary quantity of water 22 to obtain the desired final concentration of polymeric compound. Once the final concentration of buffer is reached in mixing vessel 2, commercial enzyme preparation 23 is added to mixing vessel 2. Optionally the mixture of polymeric compound 11, water 22 and commercial stabilized enzyme preparation 23 can be mixed for between 0.5 minutes and 10 minutes, preferably between 2 minutes and 5 minutes with a stainless steel impeller 21. Any desired mixing device may be used in place of the impeller 21 as desired.

Commercial enzyme preparation 23 is reformulated in the mixing vessel with, for example, between 4 parts polymeric compound and water to 1 part commercial enzyme preparation and 100 parts polymeric compound and water to 1 part commercial enzyme preparation, preferably between 4 parts polymeric compound and water to 1 part commercial enzyme preparation and 15 parts polymeric compound and water to 1 part commercial enzyme preparation. The dilute polymeric compound is advantageous in that it reduces the concentration of the polymeric stabilizers and other preservatives in which the enzyme is contained, however some stability is still imparted to the reformulated enzyme solution to reduce fouling and bacteria accumulation between the time the commercial enzyme solution is reformulated and the time that it is pumped to the bioreactor. Additionally, the dilute polymeric compound solution has a lower specific gravity than the commercial enzyme preparation 23 and has a pH similar to the pH in the bioreactor.

The reformulation ratio depends on the concentration of enzyme in the commercial enzyme preparation. Currently, concentrations of enzyme used in commercial enzyme preparations for the fuel ethanol, high fructose corn syrup and other industrial applications range from approximately 1% to 20% enzyme. In the future, higher concentrations of enzymes in commercial enzyme preparations may be used. As these concentrations increase, so too will the reformulation ratio. For example, a commercial enzyme preparation with a 75% enzyme concentration may enable a reformulation ration where 250 parts polymeric compound and water are mixed with 1 part commercial enzyme preparation.

In a preferred embodiment, the mixture of polymeric compound 11 and commercial enzyme preparation 23 can be metered, using variable speed pump 6 through a column 3 containing a metal or a metal-impregnated particulate matter 13 such that the residence time of the dilute polymeric compound-enzyme mixture in the column is, for example, between 1 and 15 minutes, preferably between 5 and 10 minutes. The metal-impregnated particulate matter can be zeolite, plastic pellets, ceramic beads, glass beads or any other material upon which metal particulate matter can be impregnated. Preferred metals include zinc, silver, copper, nickel, KDF55 and KDF85. The most preferred is KDF55. In a preferred embodiment, spent KDF55 is replaced with fresh KDF55 after between 250 gallons and 750 gallons of reformulated enzyme solution. Passing through the column 3 completes the reformulation of the enzyme and the reformulated enzyme solution 14 is collected in storage vessel 4. An optional surge tank 10 can be connected to the storage vessel 4 so that the storage vessel 4 can be emptied as desired. Depending on the rate at which the enzyme is reformulated and the rate at which the reformulated enzyme solution is added to the bioreactor 9, reformulated enzyme solution may sit in the storage vessel 4 for up to 100 hours.

Reformulated enzyme solution can be pumped to the bioreactor with a variable speed pump 7. The reformulated enzyme solution 14 can be sent to the bioreactor 9 alone or in combination with the commercial stabilized enzyme preparation 23. The ratio of reformulated enzyme solution and commercial stabilized enzyme preparation can be between 100% reformulated enzyme solution to 0% stabilized enzyme preparation and 10% reformulated enzyme solution to 90% stabilized enzyme preparation, preferably 80% reformulated enzyme solution to 20% stabilized enzyme preparation. The percentages used herein refer to the percent of non-reformulated enzyme used in a particular bioreactor prior to introduction of the present invention.

Two variable drive pumps 7 and 8 are in communication with each other and with flowmeters 27 and 28 to ensure delivery of adequate amount of enzyme to the bioreactor 9. For example, if there is a problem with variable drive pump 7, then the flowmeter 27 would communicate to the control system 18 the extent to which flow from pump 7 had slowed. Control system 18 then instructs variable drive pump 8 to take over to an extent that compensates for the decrease in flow from pump 7. This ensures that an adequate quantity of enzyme, either reformulated or non-reformulated, is continuously delivered to bioreactor 9. The apparatus is designed such that a stabilized commercial enzyme preparation can be supplied to said apparatus by a valve 17 and supply is independent of the variable drive pump 8. If there is a problem with variable drive 8, commercial stabilized enzyme can be delivered to the apparatus to continue reformulating enzyme and delivering it to bioreactor 9.

The control system 18 for the apparatus contains programmed settings for automated control of all valves and pumps associated with the apparatus and process. A computer screen provides visual cues to operators for tasks to complete such as changing metal or metal-impregnated particulate matter 13 in the column 3 and cleaning the storage tank 4.

In another embodiment of the present invention, the reformulated enzyme solution 14 is pumped through a column 3 containing a metal or metal-impregnated particulate matter 13 and directly into a bioreactor, without being stored in a storage vessel 4, as in a continuous process.

In another embodiment of the present invention, the polymeric compound and water mixture are mixed with stabilized enzyme preparation 23 in-line, using an in-line mixer and pumped directly through the column 3 containing a metal or metal-impregnated particulate matter 13 to the bioreactor, without being mixed in a mixing vessel 2 and without being stored in a storage vessel 4.

In another embodiment of the present invention, control system 18 is in communication with a central control system 19 that monitors the entire production facility. Changes in conditions within the production facility can trigger changes in the control system for the apparatus of the current invention. For example, in a fuel ethanol plant, a feedstock change from corn to milo, or from switchgrass to municipal solid waste, or corn stover, could result in changed requirements for enzyme to feedstock ratios. These ratio changes may be preset in the control system for the present apparatus. As these changes are captured in the facility data control system, automatic adjustments to the dosing regime, component inputs and ratios of reformulated enzyme to commercial stabilized enzyme can be made.

The pH should be maintained at or around the optimum pH of the enzyme. For alpha-amylase we have found that a pH between 5.5 and 6.5 is suitable, most preferably a pH of between 5.75 and 6.0. When using the present invention with alpha-amylases that have a lower pH range, the pH will be maintained in this lower range, for example 4.5 to 5.5. For glucoamylase, we have found that a pH between 4.2 and 5.0 is suitable, most preferably a pH of between 4.5 and 4.9. For cellulase, we have found that a pH between 5.5 and 6.5 is suitable, most preferably a pH of between 5.8 and 6.3.

The metal and metal-impregnated particulate matter, therefore, serve to improve the short-term stability of the reformulated enzyme solution without the salts and antioxidants present in the commercial stabilized enzyme preparations.

While it is known that KDF55 and KDF85, the preferred metal particulate matter, are known to remove chloride ions from water, to our knowledge, KDF has not been used with and is not known to be compatible with enzymes prior to the present invention. Experiments showed that KDF 55 removes between 5% and 15% of the chloride ions in the reformulated enzyme solution, even after the chloride concentration in commercial enzyme preparation is reduced via addition of dilute polymeric compound. While some metals, such as copper are known to inhibit enzymes, surprisingly the KDF did not undesirable inhibit the activity of the enzyme and provided the added benefit of reducing the chloride concentration of the reformulated enzyme solution. The metal particulate matter also imparted additional beneficial characteristics to the enzyme.

Passing the reformulated enzyme through the metal and metal-impregnated particulate matter has been shown to change the structure of the reformulated enzyme and imparts added thermostability to the enzyme. This has been shown through sedimentation velocity studies, ELISA tests and SDS Polyacrylamide Gel Electrophoresis. Sedimentation velocity studies indicate a change in Stokes radius when comparing commercial stabilized enzyme formulations and enzymes that have been reformulated according to the present invention. The Stokes radius decreases by up to 18% for reformulated alpha-amylase that is passed through KDF55. In one such study, the Stokes radius of the alpha-amylase molecule in a commercial enzyme preparation of Liquozyme SC DS was 5.1 nm whereas the Stokes radius of the alpha-amylase in Liquozyme SC DS that was reformulated according to the present invention was 4.2 nm. Therefore, passing the reformulated enzyme through a metal and a metal-impregnated particulate matter creates a more compact molecule relative to the commercial stabilized enzyme preparation from which it was produced.

ELISA tests also indicate that passing reformulated enzymes through metal and metal-impregnated particulate matter confers structural changes. Binding of an antibody to alpha-amylase is different for reformulated enzyme relative to the commercial enzyme preparation from which the reformulated enzyme came. This differential binding indicates a change in the exposed region of the alpha-amylase molecule to which the antibody binds. Compacting the enzyme, as shown in the sedimentation velocity studies would have this effect.

SDS Polyacrylamide Gel Electrophoresis (PAGE) studies confirm that the mass of the enzyme is the same before and after reformulation. However, SDS PAGE studies show that commercial enzyme preparation that is reformulated according to the present invention has less intense bands corresponding to small molecular weight proteins relative to the non-reformulated commercial enzyme preparation. This is apparent for two commercial enzyme preparations from different suppliers.

SDS PAGE also indicates that commercial alpha-amylase preparation that is reformulated according to the present invention has increased thermalstability relative to the non-reformulated commercial alpha-amylase preparation. There are fewer small molecular weight fragments in the reformulated sample than in the non-reformulated sample after heating at 91 degrees Celsius for one hour. These small molecular weight fragments have molecular weights of less than 55 kDa, the weight of the intact alpha-amylase, and are the result of thermal denaturation. This is important to the present invention because the residence time of alpha-amylases in bioreactors in many fuel ethanol plants exceeds one hour. Temperatures in these bioreactors are frequently as high as 85 degrees Celsius. Subjecting some stabilized commercial enzyme preparations to the present process can lead to the formation of ester-based or lactone-based polymers. These interfering polymers can provide a surface upon which bacterial growth is encouraged. This is one of the reasons for polymeric stabilizers. A small amount of certain polymeric compound, such as, but not limited to glycerol, propylene glycol, polyethylene glycol and alcohol ethoxylates, is used in the present reformulation process. We have found that between 2 and 25% (v/v) of the total hydration volume can be polymeric compound, and more preferably between 5 and 10% (v/v) of the total hydration volume. Thus, the dilute aqueous solution contains the polymeric compound in an amount greater than 2% and less than 30% (v/v). While the addition of polymeric compound is counter to the effort of reducing the polymeric compound concentration in the commercial enzyme preparation, the present process, even with the addition of a small amount of polymeric compounds, substantially reduces the overall concentration of these polymeric stabilizers while enabling the just-in-time reformulation to improve thermalstability and dosing accuracy.

Bacterial growth is enhanced by the presence of the lactone or ester-based polymer in the reformulated enzyme solution. Bacterial growth may also occur in the absence of these interfering polymers. Commercial enzyme preparations often contain gram positive cocci in amounts less than $1 \times 10^2$ cfu/mL. This concentration of colony forming units does not change substantially over time due to the polymeric stabilizers and other antioxidant and salt stabilizers in the commercial enzyme preparation. In contrast, reformulated enzyme, as described in the present invention develops other bacteria over time. For example, after 24 hours, both gram positive and gram negative rods are found at a concentration of $1 \times 10^2$ cfu/mL as well as a low concentration of yeast ($<1 \times 10^2$ cfu/mL). After 72 hours, both gram positive and gram negative rod populations have increased. By 120 hours after reformulating the enzyme, bacterial population has stabilized at less than $1 \times 10^3$ cfu/mL and little further growth is observed.

The temperature for the process can be any temperature at which the enzyme in question is active. The method is carried out most preferably at ambient temperature. To extend the life of the reformulated enzymes, the method can be carried out at temperature lower than ambient temperatures, most preferably at 4 degrees Celsius.

Commercial enzyme preparations are often characterized by specific gravities between 1.05 and 1.3 g/mL. Commercial enzyme preparations can be characterized by specific gravities as high 1.5 g/mL. In the case of a reformulated enzyme solution, as described in the present invention, said enzyme solution usually has a specific gravity of between 1 and 1.05 g/mL and a conductivity of between 0.1 and 10 mS/cm. Preferably, hydration results in a specific gravity of 1 g/mL. It is an object of the present invention to reduce the specific gravity of commercial enzyme preparations to 1 g/mL.

In a preferred embodiment, reformulated alpha-amylase is mixed with commercial alpha-amylase, that has been stabilized using polymeric, antioxidant and/or salt stabilizers, in a ratio of about 80% reformulated enzyme solution to about 20% stabilized alpha-amylase preparation and combined with a liquefied starch stream that may contain residual grain particles, water, thin stillage or other chemicals and process streams to promote the hydrolysis of carbohydrates.

In another embodiment of the present invention, reformulated glucoamylase is mixed with commercial glucoamylase, that has been stabilized using polymeric, antioxidant and/or salt stabilizers in a ratio of about 30% reformulated enzyme solution to about 70% stabilized glucoamylase preparation and combined with a liquefied starch stream containing maltodextrins of variable length.

In another embodiment of the present invention, reformulated cellulase is mixed with commercial cellulase that has been stabilized using polymeric, antioxidant and/or salt stabilizers in a ratio of about 50% reformulated enzyme solution to about 50% stabilized glucoamlyase preparation and combined with a liquefied cellulose stream.

The bioreactor conditions may play an important role in the effectiveness of the present invention. Use of the present invention is more effective in bioreactors where the substrate is soluble in aqueous solution. For example, in the production of fuel ethanol, reformulation of alpha-amylase according to the present invention is more effective in the liquefaction system where substrate is predominantly soluble, long-chain maltodextrins as compared to the slurry system where the substrate is predominantly insoluble starch granules. While effectiveness is relatively lower in the slurry, there is still an advantage to adding some reformulated alpha-amylase to the slurry system in combination with non-reformulated commercial enzyme preparation.

The present invention, as described above provides a process and an apparatus to overcome difficulties faced by users of commercial enzyme preparations relating to high concentrations of polymeric stabilizers, salts and antioxidants and the related mechanical difficulties of accurately pumping high specific gravity solutions to bioreactors. Overcoming these difficulties must be done in a just-in-time fashion to eliminate negative effects, such as bacterial growth and enzyme agglomeration, related to reformulating these commercial enzyme preparations.

Lab-Scale Activity Assays

Commercial enzyme preparation was reformulated according to the invention. Specifically the reformulation used 10 mL dilute propylene glycol mixed with 1 mL of commercial enzyme preparation. Enzyme activity was verified after reformulation using the Phadebas colorimetric enzyme assay kit.

Comparison of enzyme concentrations for two reformulated samples and a commercial enzyme preparation (not reformulated).

| Sample | Enzyme sample | Enzyme Concentration |
|---|---|---|
| A | Reformulated sample, according to invention | 1.50 mg/ml |
| B | Reformulated sample, according to invention | 1.45 mg/ml |
| C | Commercial Enzyme Preparation (not reformulated) | 14.91 mg/ml |

Comparison of enzyme activities for reformulated enzyme samples and a commercial enzyme preparation (not reformulated),

| Sample | Enzyme sample | Enzyme Activity |
| --- | --- | --- |
| A | Reformulated sample, according to invention | 25 μkat/L |
| B | Reformulated sample, according to invention | 24 μkat/L |
| C | Commercial Enzyme Preparation (not reformulated) | 30 μkat/L |

Clearly, the non-reformulated commercial enzyme preparation has higher activity than the reformulated enzymes in the lab-scale assay.

The activity assay was done at 37 degrees C., in 90 mM sodium phosphate buffer (pH 5.5) according to the Phadebas alpha-amylase assay protocol: One tablet of Phadebas® Amylase Test kit (Magle Life Sciences; Art. No. 1301; Batch No. 8M5007) was added to 4 ml of dH$_2$O in each tube of fifteen 15-ml polypropylene tubes (BD Falcon; Ref #352096) using forceps. The tubes were incubated with mixing using a Fisher Roto Rack Model 96 at 37° C. in a warm room for 1 hr. 200 μl of each different concentration of IMM amylase sample E (see table 1 above) or dH$_2$O (as a blank) in triplicate were added to each conical tube. The sample- and blank-containing conical tubes were incubated at 37° C. (warm room) for exactly 15 minutes then 1 ml of 0.5 M NaOH was added to stop the reactions. The samples were centrifuged at 2800 rpm in a Beckman GSR centrifuge for 10 min Since the blue-coloured supernatants of the centrifuged samples were quite dark, 400 μl aliquots were diluted to 4 ml with dH$_2$O. The diluted supernatants were added to 1-cm pathlength disposable cuvettes (Evergreen Scientific; cat #201-3124-010) and their absorbances were measured at 620 nm against dH$_2$O using a Gilford model 250 UV/Vis spectrophotometer. The average absorbance values of the blanks were subtracted from those of the samples, taking into account the dilutions made. The α-amylase activity of the sample (both in U/L and μkat/sL) was determined from the standard curve and from a linear regression analysis.

Example 1

A reformulated enzyme solution was obtained by mixing 1 part Liquozyme SC DS, a stabilized alpha-amylase preparation from Novozymes, 9 parts water and 1 part propylene glycol at room temperature. This served to reduce the concentration of polymeric stabilizers as well as to reduce the concentration of salts and antioxidants. The inclusion of propylene glycol provides enough stability so that the enzyme solution can remain in a vessel until it is used, up to 100 hours. Said reformulated enzyme solution was passed through a column containing KDF-55, a copper-zinc alloy, and pumped to a vessel. Under normal operating conditions pure, non-reformulated Liquozyme SC DS with an alpha-amylase concentration of about 15 mg/mL is added to slurry and liquefaction tanks in a dry mill fuel ethanol plant at 68 ml/min (1020 mg/min) and 90 ml/min (1350 mg/min) respectively. In this example, 68 mL/min (1020 mg/min) of pure Liquozyme SC DS was added to the slurry tank; no change from normal operating conditions. However, to the liquefaction tank, reformulated enzyme, according to the present invention, was added at 65 mL/min (89 mg/min) and pure Liquozyme SC DS was added at 25 mL/min (375 mg/min) While the volume of the reformulated enzyme and pure Liquozyme SC DS was maintained at 90 mL/min, the actual mass of enzyme flowing to the liquefaction tank was 464 mg/min (375 mg/min of pure Liquozyme SC DS and 89 mg/min of enzyme contained in the 65 mL/min reformulated enzyme). This represents a decrease in required enzyme to the liquefaction system of 66% and substantial savings to the ethanol producer.

Under normal conditions, the enzyme supplier recommends adding to the slurry and liquefaction bioreactors of a dry mill fuel ethanol plant a dose of 0.02 and 0.022% (w/w) (weight Enzyme/wet weight feedstock). In plants that run a mixture of milo and corn, the enzyme supplier recommends a stronger dose, i.e. greater than 0.022% enzyme/wet corn and milo mixture (w/w). Under conditions listed above, the ratio of the weight of alpha amylase relative to the weight of the corn and milo mixture added to the liquefaction and slurry bioreactors was 0.017%. Assuming the supplier's recommended dosing is 0.024%, the present invention reduced the total enzyme dose by 29%. This is a significant savings for ethanol producers.

Results from experiments described in EXAMPLE 1 show no change in the pump pressures on the pumps that deliver the mash to downstream bioreactors, a common measurement of mash viscosity in fuel ethanol plants. Most importantly, the average ethanol yield/bushel of feedstock, which ethanol plants use to measure productivity, was statistically equivalent.

To validate results, 0.017% (weight of enzyme/weight of corn and milo mixture) of the commercial enzyme formulation was added to the liquefaction bioreactor. This reduction in enzyme flow to the liquefaction bioreactor specifically, resulted in a faster than normal increase in the viscosity of the starch slurry. This viscosity increase began to reduce the flow of liquefied starch to downstream bioreactors. The trial was terminated early for fear of process upsets.

While the claimed invention has been described in detail and with reference to specific embodiments thereof, it will be apparent to one of ordinary skill in the art that various changes and modifications can be made to the claimed invention without departing from the spirit and scope thereof.

The invention claimed is:

1. A method of producing alcohol or sugar in a commercial-scale bioreactor comprising:
   mixing a commercial enzyme preparation comprising at least one group 3 hydrolase, that has been stabilized for shipment or storage, with a dilute aqueous solution comprising a polymeric compound in a mixing vessel in a ratio of 1 part commercial enzyme preparation to at least 4 parts of the dilute aqueous solution to form a diluted enzyme solution;
   passing the diluted enzyme solution through a chamber containing at least one metal particulate matter or metal-impregnated particulate matter to produce a reformulated enzyme solution; and
   within 100 hours of production of the reformulated enzyme solution, transferring at least a portion of the reformulated enzyme solution to a commercial-scale bioreactor containing at least 20,000 gallons of at least one of starch or cellulose to produce an alcohol or sugar, wherein a total amount of enzyme in the form of the reformulated enzyme solution added to the bioreactor is at least 20% less than the amount of enzyme in the form of the commercial enzyme preparation that would have been required to produce an equivalent amount of alcohol or sugar.

2. The method according to claim 1 wherein the metal particulate matter comprises at least one of silver, zinc, nickel, copper, KDF55, KDF85.

3. The method according to claim 1, wherein the metal impregnated on the metal-impregnated particulate matter comprises at least one of silver, zinc, nickel and copper.

4. The method according to claim 1, wherein the metal impregnated particulate matter comprises at least one of zeolite, plastic pellets, ceramic and glass beads.

5. The method according to claim 1, wherein the bioreactor comprises at least one of a slurry system, a pre-treatment system, a liquefaction system, a saccharification system, or a fermentation system.

6. The method according to claim 1, further comprising supplying at least one of starch, maltodextrin, cellulose or xylose to the bioreactor so that the bioreactor contains at least one of the starch, maltodextrin, cellulose or xylose.

7. The method according to claim 1 wherein the reformulated enzyme solution is mixed with commercial enzyme preparation in a ratio of between 15% reformulated enzyme solution and 85% commercial enzyme preparation from which the reformulated enzyme solution is derived and 100% reformulated enzyme solution and 0% commercial enzyme preparation from which said reformulated enzyme solution is derived.

8. The method according to claim 1, wherein grain syrup comprising at least one sugar is produced.

9. The method according to claim 1, wherein alcohol is produced.

10. The method according to claim 1, further comprising reformulating the commercial enzyme preparation with between 4 parts dilute aqueous solution to 1 part commercial enzyme preparation and 100 parts dilute aqueous solution to 1 part commercial enzyme preparation.

11. The method according to claim 1, wherein the polymeric compound comprises at least one of propylene glycol, (poly)ethylene glycol, PEG(20)sorbitan monolaurate, glycerol and an alcohol ethoxylate and the dilute aqueous solution comprises the polymeric compound in an amount between 2% and 25% (v/v) in water.

12. The method according to claim 1, wherein the reformulated enzyme solution is pumped continuously to a bioreactor from the mixing vessel and is not stored in a storage vessel.

13. The method according to claim 1, wherein the reformulated enzyme solution has specific gravity of about 1 g/mL.

14. The method according to claim 1, wherein the reformulated enzyme solution has increased thermalstability at about 90 degrees Celsius.

15. The method according to claim 1, wherein the Stokes radius of the reformulated enzyme is less than the Stokes radius of the commercial enzyme solution from which it was derived.

16. The method according to claim 1 wherein the chloride concentration in the reformulated enzyme is decreased, relative to the commercial enzyme preparation by a factor equal to the degree of dilution in the dilute enzyme solution plus an additional 5 to 15%.

17. The method according to claim 1, wherein the total amount of enzyme in the form of the reformulated enzyme solution added to the bioreactor is at least 40% less than the amount of enzyme in the form of the commercial enzyme preparation that would have been required to produce an equivalent amount of alcohol or sugar.

18. The method according to claim 1, wherein the total amount of enzyme in the form of the reformulated enzyme solution added to the bioreactor is at least 60% less than the amount of enzyme in the form of the commercial enzyme preparation that would have been required to produce an equivalent amount of alcohol or sugar.

19. A method of producing alcohol or sugar in a commercial-scale bioreactor comprising:
    mixing a commercial enzyme preparation comprising at least one group 3 hydrolase, that has been stabilized for shipment or storage, with a dilute aqueous solution comprising a polymeric compound in a mixing vessel in a ratio of 1 part commercial enzyme preparation to at least 4 parts of the dilute aqueous solution to form a diluted enzyme solution;
    passing the diluted enzyme solution through a chamber containing at least one metal particulate matter or metal-impregnated particulate matter to produce a reformulated enzyme solution having increased enzyme activity compared to the commercial enzyme preparation; and
    within 100 hours of production of the reformulated enzyme solution, transferring at least a portion of the reformulated enzyme solution to a commercial-scale bioreactor containing at least 20,000 gallons of at least one of starch or cellulose to produce an alcohol or sugar.

20. The method according to claim 19, wherein the increased enzyme activity is defined by an increase in the rate at which substrate is converted to product, per unit mass of enzyme used.

* * * * *